United States Patent [19]

Bartha et al.

[11] 4,304,118

[45] Dec. 8, 1981

[54] PROCESS AND EQUIPMENT FOR THE THERMAL ANALYSIS OF MATERIALS

[75] Inventors: László Bartha; Csaba Lénárt; Károly Németh; Elemér Nagy, all of Budapest, Hungary

[73] Assignee: Magyar Tudomanyos Akadémia Müszaki Fizikai Kutató Intézete, Budapest, Hungary

[21] Appl. No.: 91,357

[22] Filed: Nov. 5, 1979

Related U.S. Application Data

[63] Continuation of Ser. No. 895,985, Apr. 13, 1978, abandoned.

[30] Foreign Application Priority Data

Apr. 14, 1977 [HU] Hungary .......................... MA 2868

[51] Int. Cl.³ .............................................. G01K 17/04
[52] U.S. Cl. .................................................. 73/15 B
[58] Field of Search ........................... 73/15 B, 190 R

[56] References Cited

U.S. PATENT DOCUMENTS

| | | | |
|---|---|---|---|
| 3,055,206 | 9/1962 | Watson et al. | 73/15 |
| 3,172,493 | 3/1965 | Van Koch et al. | 73/15 X |
| 3,263,484 | 8/1966 | Watson et al. | 73/15 |
| 3,271,996 | 9/1966 | Paulik et al. | 73/15 |
| 3,477,274 | 11/1969 | Wald et al. | 73/15 |
| 3,527,081 | 9/1970 | Hill | 73/15 |

OTHER PUBLICATIONS

Hogan et al., "Apparatus for Observing Physical Changes at Elevated Temperatures", in Analytical Chemistry, vol. 32#4, 4/60, pp. 573, 574.
Hill et al., "Infrared Heating Applied to D.T.A.", in Analytical Chemistry vol. 31#8, 8/59, pp. 1443, 1444.

Primary Examiner—Herbert Goldstein
Attorney, Agent, or Firm—Gabriel P. Katona

[57] ABSTRACT

A method and an apparatus for the differential thermal analysis of materials includes heating a first sample to be investigated and a reference sample by radiation heat transfer from respective separated radiation sources, controlling both sources according to a predetermined temperature program for the samples, interposing an element that partly transmits radiation between each of the samples and their associated sources, sensing the temperature difference between the elements, controlling one of the radiation sources in response to the temperature difference to equalize the temperature of the elements and measuring the temperature difference between the samples during the temperature program.

17 Claims, 7 Drawing Figures

PROCESS AND EQUIPMENT FOR THE THERMAL ANALYSIS OF MATERIALS

Continuation of Ser. No. 895,985 filed on Apr. 13, 1978, now abandoned.

The object of the invention is a process and an apparatus for the thermal analysis of materials and with which thermogravimetry /TG/, differential thermogravimetry /DTG/, thermal analysis /TA/ and differential thermal analysis /DTA/ investigations of material samples can be carried out.

Differential thermogravimetry /DTG/ determining the rate of mass change, and thermogravimetry /TG/ are measuring methods used for the examination of physicochemical changes consequent upon a mass change and taking place under the effect of a temperature change. Numerous types of equipments, so-called thermobalances are known for such investigations.

The transformations taking place under the effect of temperature changes, whether they are incidental to mass changes or not, like phase transformation, result also in a heat-content change of the material. Depending on the degree and direction of this content change, the temperature of the sample surroundings also changes. This temperature change is determined by thermal analysis, generally in the following way: two sample holders containing respectively the material to be examined and some reference material, in which latter no thermal change occurs in the investigated temperature range, are heated up in an identical way, and the temperature difference between them is measured. A difference appears if a process consequent to a heat-content change of the material to be examined takes place. In view of the above measurement setup, this process is called differential thermal analysis /DTA/. Such equipments are known.

Equipments which simultaneously meet both types of thermal investigation requirements, are known as well which thus carry out TG-DTG-DTA examinations.

Differential thermal examinations require that two sample holders, one of which is connected to one of the arms of a balance in the DTG case, are heated up in the same way.

In most known equipments, this requirement is met by placing the sample holders one beside the other in the chamber of an adjustable furnace, thus both sample holders are affected to the same extent by a temperature change of the furnace. This method has several drawbacks. The internal furnace chamber is relatively large, consequently its thermal inertia is large; thus, the speed of regulation of the system is limited. Due to gas convection and radiation—especially at higher temperatures—it is hard to ensure the same thermal condition to both sample holders. Another disadvantage is that the two sample holders are necessarily in an identical phase environment.

In other known equipments, each sample holder has it own heating element, and identical heating is ensured by regulation with electric signals received from heat detectors of the sample holders. The disadvantage of that solution is that the temperature change caused by the process taking place in the sample holder reacts on the heating regulation system.

The sample holders of such systems can be located separately, this enables their gas surroundings to be different; their drawback, however, is that each sample holder and its related heater are in an identical environment, and this is why heater-corrosion sensitivity limits the possible atmosphere. Moreover, in known equipments of this type the heating elements are heated by resistances that necessarily limit the maximal rate of the temperature change of the "heating element-sample holder" complex.

The process and equipment of this invention are apt to eliminate the mentioned disadvantages.

According to the invention, during the thermal analysis of a material, the heating of the sample to be investigated is carried out by heat transfer occurring by means of radiation. With this process, very quick measurements can be taken since the time constant of the heating system is much smaller than those of known equipments; on the second hand, it becomes possible to increase the measuring accuracy by additional measurements of radiation intensity and by regulating the heating accordingly. Another advantage is that the heating equipment does not load down the balance in case of a thermogravimetric equipment.

The equipment according to the invention is used for thermal analysis of materials. It includes a sample holder to lodge the material to be investigated, the heating equipment of the sample holder and a heat or temperature detector to measure the sample temperature. It is characterized in that the heating equipment contains at least one lamp and an optical system that directs the radiation emitted by the lamp on the sample and/or the sample holder.

In a preferred embodiment, an optical filter is located between the lamp and the sample holder for filtering out the visible radiation or part of it.

In this same especially recommended structure, there is an element partly transparent to the radiation, located between the sample holder and the lamp. The element is provided with a temperature detector to measure the intensity of the radiation emitted by the lamp toward the sample holder. It may be a half-transparent plate, a metallic porous or perforated plate or a net.

In an embodiment of the inventive equipment suitable for differential thermo-analysis, the equipment includes at least two sample holders, provided with temperature detectors and used to lodge one reference sample and at least one sample to be investigated. There are lamps and optical systems to heat the sample holders, and elements provided with temperature detectors; the detectors of the sample holders are connected to an apparatus which measures and/or records the temperature difference between one of the sample holders and the others. The detector of the first sample holder is connected, on the one hand, to a supply source through a controller for feeding the lamp that corresponds to the sample holder and, on the other hand, to a supply source through a summing unit the lamp that corresponds to the other sample holder. A program generator is connected to the second input of the controller. Moreover, the temperature detector of the element corresponding to the other sample holder is connected to another controller, while the detector of the element that corresponds to the first sample holder is connected to the second input of the other controller, the output of which is in turn connected to the second input of the summing unit.

This solution makes possible the construction of a very accurate equipment with a very good base line, and in which the thermal changes taking place in the sample do not react on the heating that is controlled by the specified program.

According to the invention, the accuracy of the equipment can be further increased if the other controller is provided with a third input to which the output of a function generator is connected, while the input of the latter is connected to an adjusting signal source and/or to the output of the program generator.

In the embodiment according to the invention which is suitable for thermogravimetry, the single sample holder lodging the sample to be investigated, or one of the several sample holders is fixed to an arm of a balance.

Preferably the balance has electromechanical means to ensure moment compensation, a differential capacitor to detect a displacement of the balance arm, as well as a regulating means inserted between the differential capacitor and the electromechanic means.

In the following, the equipment according to the invention is described by way of an example on the basis of embodiments illustrated in the accompanying drawings, wherein.

Figure 1:
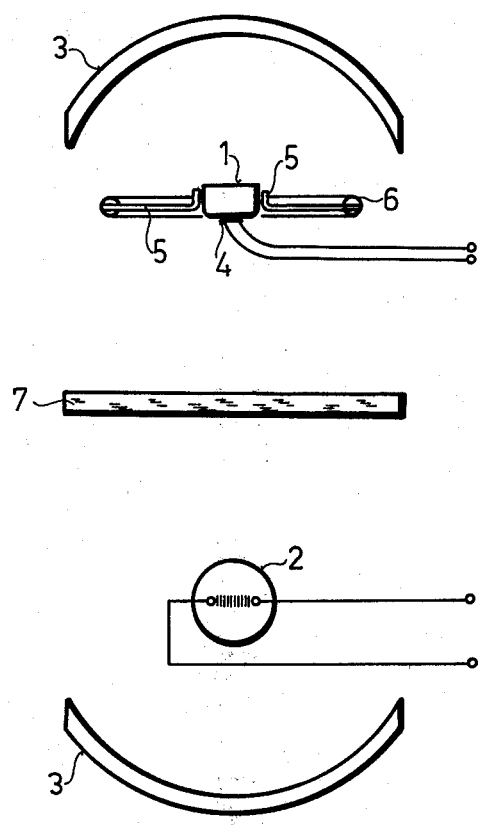
FIG. 1 is schematic drawing of a single heating arrangement and of a sample holder of the equipment according to the invention.

In FIG. 1, a schematic drawing of a sample holder 1 of the equipment according to the invention and of its corresponding heating equipment is shown. The sample holder 1 is made of a material with, as far as possible, low heat capacity, good thermal conductivity and small specific heat—e.g. platinum—and is provided with a heat or rather temperature detector 4.

The heating equipment includes an electric lamp 2 and an optical system 3 to direct the radiation emitted by the lamp 2 onto the sample holder 1. The optical system 3 may consist e.g. of one or two mirrors with a /preferably elliptical/ concave surface. The heat detector 4 is simply a thermocouple made of a thin wire for low heat dissipation, and is soldered to the side of the sample holder 1 which is opposite to the sample.

In order to reinforce the sample holder 1 and for the sake of the low heat dissipation, two or three thin supporting wires 5 of poor heat conductivity and high strength are fixed /soldered/ to the sample holder 1 and to a structure 6 encircling the sample holder, e.g. an arm. The radiation emitted by the lamp 2 is directed onto the sample holder 1 so that it reaches it in a homogeneous beam and, on the other hand, warms up the wires of the detector 4 in the same way as it warms up the wires 5 and the sample holder 1.

In a modified embodiment, the sample holder may be held by the wires of the thermocouple (detector) soldered to it.

The visible range of the radiation emitted by the lamp 2 or its higher energy part may have an undesirable influence on the course of certain processes. In order to eliminate such an additional effect, an optical filter 7 which filters the visible light or its undesirable part may be placed between the sample holder 1 and the lamp 2. This filter 7 is not shown in the remaining embodiments.

Figure 2:
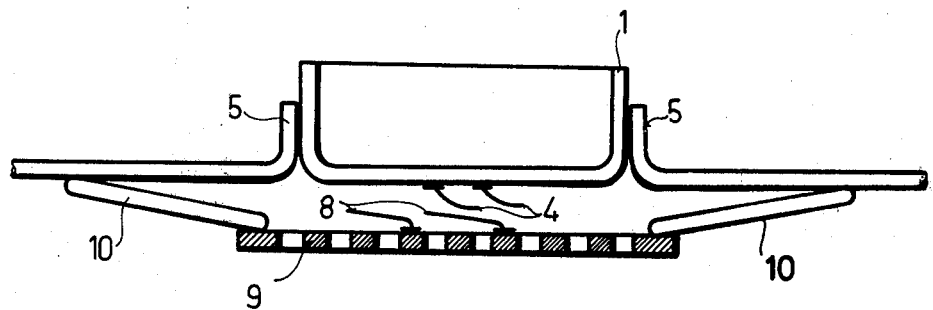
FIG. 2 is a sectional view of a preferred sample holder of the equipment.
Figure 3:
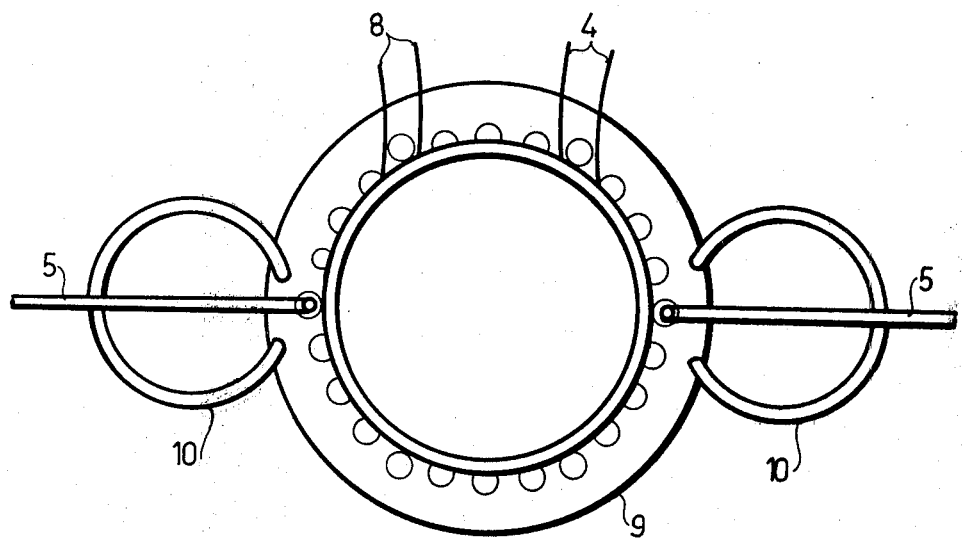
FIG. 3 is a top view of the sample holder according to FIG. 2.

In FIGS. 2 and 3, it is suggested to put an element 9 between the sample holder 1 and the lamp 2, provided with a temperature detector 8, and which element partly transmits and partly absorbs radiation, thus getting warmed up. The element 9 is preferably a half-transparent plate with low reflection or a metallic, finely structured, perforated plate or net. The detector 8 may be e.g. a thermocouple soldered onto the element 9. It is expedient to locate the element so that it warms up like the sample holder 1, i.e. to fix it close or adjacent to the sample holder with wires 10 that may be soldered directly to it.

Figure 4:
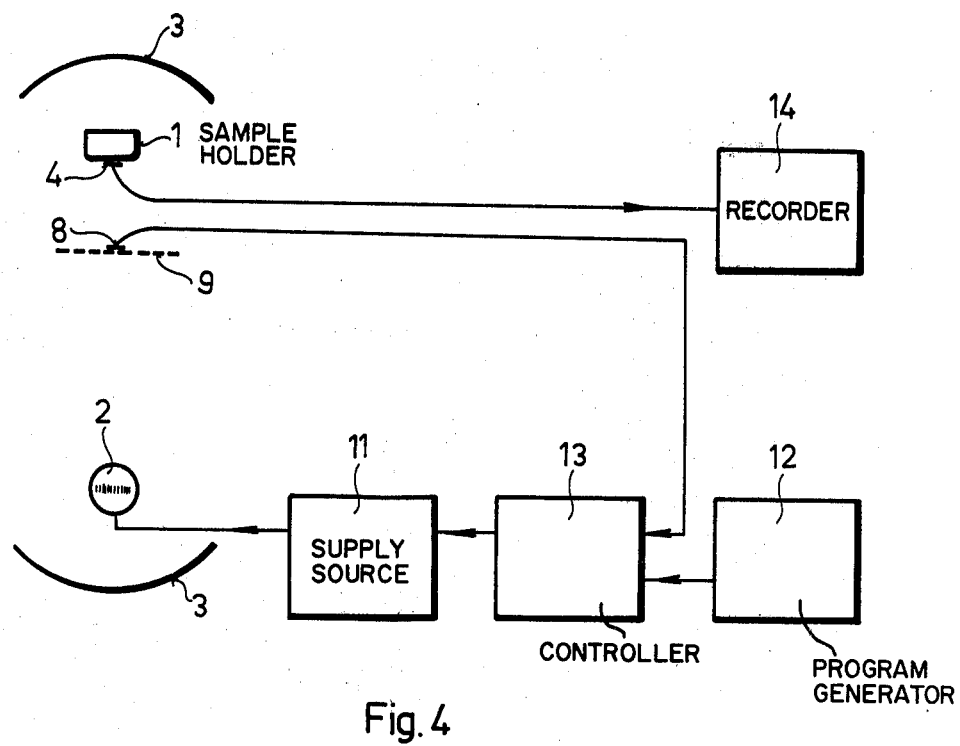
FIG. 4 is a block diagram illustrating the operation of the equipment containing the sole sample holder of FIGS. 2 and 3.

In the equipment illustrated in FIG. 4, the detector 8 of the element 9 is connected to a regulator or controller 13 acted upon by a program generator 12 and coupled to the input of a supply source 11 that feeds the lamp 2; therefore, the element 9 regulates the intensity of the radiation emitted by the lamp 2, which reaches and heats the sample holder 1.

The temperature of the sample located in the sample holder 1 of such an equipment can be measured by a measuring and/or recording apparatus 14 coupled to the detector 4 that corresponds to the sample holder 1. The element 9 is preferably placed between the sample holder 1 and the lamp 2 so that it is thermally insulated from the sample holder, i.e. the thermal process takes place in the sample put in the sample holder but does not affect temperature regulation, and vice versa, the controller 13 does not influence the measurement nor the recording of the thermal process taking place in the sample.

It ensures reproducible circumstances, with the further advantages that it does not cause an additional time constant, time delay nor dead time and that, by means of the time constant which is of the order of a second, it makes possible the formation of a regulation circuit that possesses extraordinarily quick and good dynamic properties.

Figure 5:
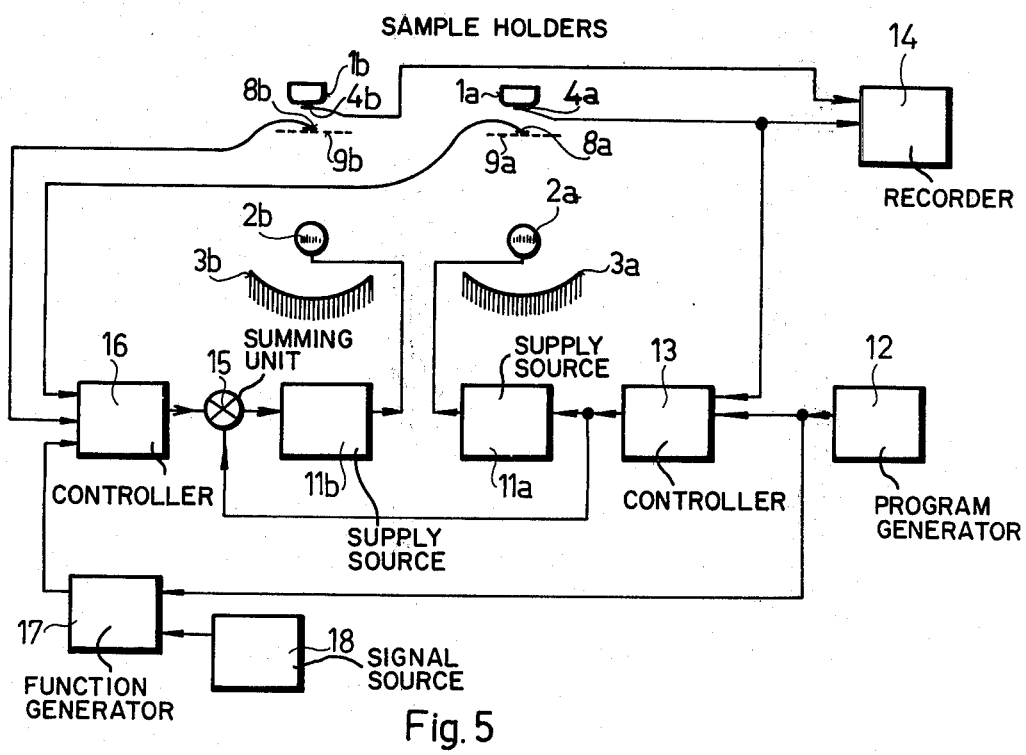
FIG. 5 shows a schematic structure and a simplified block diagram of the equipment according to the invention, fitted with two sample holders suitable for DTA measurements.

The equipment suitable for differential (DTA) measurements, shown in FIG. 5, consists of at least two identically structured sample holders 1a, 1b with temperature detectors 4a, 4b, lamps 2a, 2b and optical systems 3a, 3b corresponding to them, as well as elements 9a, 9b provided with temperature detectors 8a, 8b and located between the sample holders and the corresponding lamps.

For such embodiment, the reference sample is generally located in one of the sample holders, 1a, while the sample to be examined is in the other one, 1b. It is recommended to change the temperature of the reference sample according to a specified program in such a way that the detector 4a fixed to the sample holder 1a and the program generator 12 is connected to the controller 13, itself coupled to the input of a supply source 11a feeding the lamp 2a. It is convenient that the output of the same controller 13 be coupled through an integrator or summing unit 15 to a supply source 11b that feeds the lamp 2b which heats the other sample holder 1b.

The temperature detectors 4a, 4b of the sample holders are coupled to the apparatus 14 for measuring and/or recording the temperature difference between the sample holders 1a, 1b. In case of perfect symmetry, the temperatures of the sample holders 1a, 1b are always identical when empty; in practice, however, it is hard to ensure this.

In order to decrease differences, according to the invention, the detectors 8a, 8b of the elements 9a, 9b, located between the sample holders 1a, 1b and their respective lamps 2a, 2b are connected to two inputs of another controller 16, the output of which is coupled to the summing unit 15. In this arrangement, the radiation reaching the sample holders is made uniform by adjusting the temperature of the elements 9a, 9b to identical values; this is achieved by influencing the supply of the lamp 2b by means of regulating the supply source 11b through the controller 16 and the summing unit 15.

The aim, however, is the identity of the sample-holder temperatures; in order to compensate any remaining asymmetry, a function generator 17 is coupled to the third input of the other controller 16 and connected to the program generator 12 and/or to an adjustable signal source 18. The program generator 12, which controls the course of the sample-holder temperatures, decreases the temperature-dependent deviation of the sample holder temperatures through the function generator 17 with a base-line correction signal depending on the adjusted temperature. A base-line offset correction signal that does not depend on temperature is provided for the function generator 17 by the signal source 18.

In the arrangement corresponding to FIG. 5, there can be more than two sample holders. In this case, too, the sample holder contains the samples to be investigated. Then, the necessary number of lamps 2b, elements 9b, supply sources 11b, summing units 15, controllers 16, and, in some cases, of function generators 17 and signal sources 18, corresponds to the number of the other sample holders. Furthermore, the equipment has to contain a multi-channel measuring and/or recording apparatus in lieu of the described apparatus 14, or several single-channel apparatuses.

Figure 6:
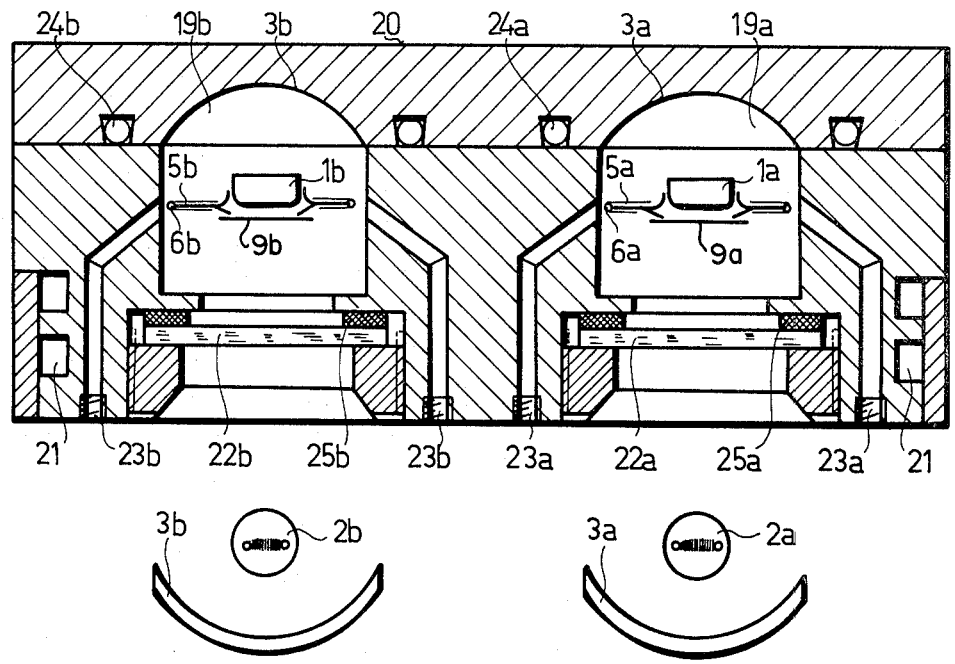
FIG. 6 is a schematic longitudinal sectional view of sample spaces of the equipment, containing two sample holders.

In FIG. 6, another embodiment of an equipment containing at least two sample holders is shown with the structure described above. It is possible here to separate the sealable spaces of the sample holders 1a, 1b and, consequently, of the samples to be examined. In order to ensure identical conditions for the sample holders, it is suggested to form separate, closed spaces 19a, 19b in a thermally well conductive block 20 closed by rubber seals 24a, 24b, the block temperature being maintained at a constant low value e.g. by cooling, such as water flowing through channels 21. The low ambient temperature of the sample holders 1a, 1b ensures good heat transmission and, thereby, quick cooling and stabilization.

To each sample holder space (19a, 19b) corresponds at least one window 22a, 22b with a rubber seal 25a, 25b that transmits radiation from the lamps 2a, 2b, and may play the role of the optical filter (7 in FIG. 1), filtering part of the radiation emitted by the lamp. A necessary number of exhaust outlets 23a, 23b are provided that make possible the evacuation of the sample spaces 19a, 19b or their flushing with gas. In such separate sample spaces, processes can be compared that take place in the same material but are placed in different gas atmospheres. A comparison of the so far described embodiments will clarify that the embodiment of FIG. 6 has two sets of the reinforcing wires, numbered 5a, 5b, as well as similar double arrangement of structures 6a, 6b that encircle the sample holders 1a, 1b. The elements 9a, 9b are also shown in FIG. 6.

The modification of the above equipment which contains two sample holders is especially suitable for differential thermal analysis /DTA/. The possible examination speed and the solutions applied here, however, make possible more diversified methodologies which yield more information than the investigative methods applied with the earlier known apparatuses.

Figure 7:
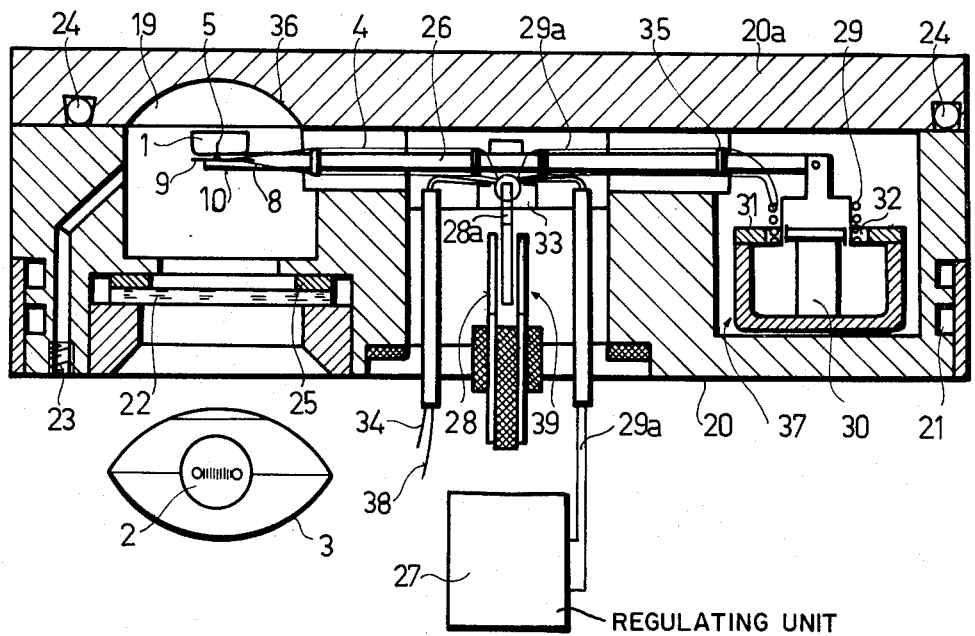
FIG. 7 is a schematic longitudinal sectional view of a sample holder fixed to a balance arm, and of a balance of the equipment, with separate sample spaces and suitable for thermogravimetric measurements.

The suggested forms of the invented sample holder and heating system led the inventors to fix the single sample holder or, when there are several ones, one of them to an arm of a balance 26 as shown in FIG. 7 in order to measure temperature-dependent mass changes /thermogravimetry, TG/. In this case heating is such that only the sample to be measured is put on the balance while the reference sample—in which mass changes may occur that disturb the measurement evaluation—is in a sample holder independent from the investigated sample. Neither the reference sample nor the heating element of the sample holder constitute loads on the balance—contrary to known equipments.

The balance arm 26 used in the equipment of FIG. 7 may be connected to a compensating electromechanical organ which is coupled, through an electronic regulating unit 27, to a member that detects balance displacements, i.e. a differential capacitor 39. It is not only easy to construct such a capacitor, it also makes possible a very good restoring precision and sensitivity.

In an experimental embodiment of the equipment according to the invention two sample holders have been used which are 8.5 mm diameter and 3 mm high dishes deep-drawn from 0.1 mm thick platinum plates, while the heat detectors 4 are 0.05 mm diameter, chromel-alumel thermocouples spot-welded to the bottoms of the dishes. The lamps 2 are 8 V, 50 watt, projection bulbs assembled with elliptical mirrors. They are located under windows 22, with rubber seals 25, the water-cooled aluminium block 20 containing the sample holders. The windows are made of 2 mm thick quartz glass or of UG6-type optical filter glass. The last UG6 window filters the whole visible range and results in an appr. 30% output decrease at the maximum accessible temperature.

Referring again to FIG. 7, the element 9 located between the sample holder 1 and its lamp 2 is an 11 mm diameter disc made of a 0.1 mm thick platinum plate. It contains 127 holes with 0.5 mm diameter and 0.8 mm mean distance, set up in the shape of a hexagon. The temperature detector 8 of the element 9 is also a chromel-alumel thermocouple, soldered to the side of the sample holder. The distance between the sample holder 1 and its corresponding element 9 is 0.8 mm.

The fork-shaped balance arm 26 which carries the sample holder 1 (toward the left-hand end) is made of a low thermal expansion, 36% Ni-content steel. It is located at a place shielded from radiation. 0.5 mm thick platinum wires 5 soldered perpendicularly to the arm 26 maintain, first, the sample holder 1 soldered to it, second, the perforated plate forming the element 9, through two, 0.3 mm thick platinum wires 10.

The second arm of the 100 mm long, two-arm balance (to the right) is fixed to electromechanical means 37 which is preferably an electrodynamic type current-force transformer. Its coil 29 moves in an air slot 32 of yokes 31 of a permanent magnet 30 fixed to a cavity in the block 20; under the effect of about 10 MA, it exerts a counter-moment that compensates the allowed 1 g load. A 15×15 mm² detecting plate 28a fixed to the balance 26 is located at a 20 mm mean distance from a balance edge bearing 33. The detecting plate moves between fixed plates 28 of identical dimensions of the capacitor 39, ensuring position detection.

The thermocouples forming the detectors 4 and 8 are led to the rotational axis of the balance 26, i.e. to the holding arm attach with the distance elements 35 that insulate outputs 34, 38, and outputs 29a of the moving coil 29. The thermocouples (4,8) are coupled to the outputs with the smallest possible moment, in a known way. In a cover 20a of the 200 mm diameter block 20 containing the sample holder 1, there are two built-in, rubber seals 24 closing a single sample space 19, as well as a concave, reflecting, spherical surface 36 shaped in the cover 20a. The surface is part of the optical system 3. In sample space 19, there are two flushing or exhaust outlets 23, one of them being shown in FIG. 7.

In a preferred embodiment of the equipment according to the invention, a temperature up to 750° C. can be reached in the air with 1 at pressure, applying quartz-glass windows. At a cooling and heating rate of 50° C./min the reproducibility of the regulation is better than 0.1° C.; if the sample holder is empty or contains a neutral material, synchronism of the temperatures of the two sample holders is better than ±0.15° C. Under the effects of temperature-dependent air convection and, at higher temperatures, of thermal expansion, the balance measures with a ±25 microgramme reproducibility in case of an empty sample holder, between 20° and 750° C. and at 1 at air pressure. Moreover, an appr. 0.5 mg maximal systematic and corrigible measuring error can be observed. The thermal time constant is about 8 seconds during spontaneous cooling under the above described circumstances.

What we claim is:

1. A method for the differential thermal analysis of materials, comprising the steps of: heating a first sample to be investigated and a reference sample by radiation heat transfer from respective radiation sources separated from each other; controlling both sources according to a predetermined temperature program for the respective samples; interposing an element that partly transmits radiation between each of the samples and the respective associated source; sensing the temperature difference between the elements; additionally controlling one of the radiation sources in response to the temperature difference so as to equalize the temperature of the elements; and measuring the temperature difference between the samples during the temperature program.

2. The method as defined in claim 1, wherein said heating step is carried out with focused beams of radiation sources, the beams having dimensions at least as large as those of respective holders provided for the samples.

3. The method as defined in claim 1, further comprising the step of measuring the change of mass of the first sample during the temperature program.

4. An apparatus for the differential thermal analysis of materials, comprising: sample holders for lodging a first sample to be investigated and a reference sample; respective radiation sources for heating said holders; respective elements interposed between said holders and said sources, for partly transmitting the radiation of the respective sources to the respective samples in their holders; first means for controlling said sources so as to vary the temperature of said holder for the reference sample according to a predetermined temperature program; second means for additionally controlling said source for the first sample so as to equalize the temperature of said elements; and means for measuring the temperature difference between said holders.

5. The apparatus as defined in claim 4, wherein said radiation sources include respective lamps and corresponding optical systems for focusing the emitted radiation onto the respective holders.

6. The apparatus as defined in claim 5, further comprising at least one optical filter interposed between one of said lamps and the respective holder, for filtering out at least a part of the visible radiation.

7. The apparatus as defined in claim 5, wherein said temperature-difference measuring means includes respective temperature detectors adjacent said holders; and a measuring unit connected to said detectors for measuring temperature differences.

8. The apparatus as defined in claim 7, wherein said control means include a program generator that provides an output signal according to the temperature program; respective controlled supplies for feeding said lamps; a summing unit having an output connected to a control input of one of said supplies and two inputs; a first controller having a first input connected to one of said detectors, a second input connected to said program generator and an output connected both to a control input of the other of said supplies and to one of said inputs of the summing unit; means for sensing the temperature difference between said elements; and a second controller having an input connected to said sensing means and an output connected to another input of said summing unit.

9. The apparatus as defined in claim 8, wherein said sensing means includes third and fourth temperature detectors respectively adjacent said elements for the first sample and for the reference sample.

10. The apparatus as defined in claim 8, wherein said second controller has a further input; and further comprising a function generator, said function generator having an input connected to said program generator and an output connected to said further input of the second controller.

11. The apparatus as defined in claim 4, further comprising a balance for continuously measuring the change of mass of the first sample.

12. The apparatus as defined in claim 11, wherein said balance includes a pivoted arm, to one end of which said holder for the first sample is fixed; a tongue fixed to said arm; a differential capacitor for detecting displacements of said tongue; electromagnetic means for producing a compensating force at the other end of said arm; and regulating means electrically connected between said electromagnetic means and said capacitor.

13. The apparatus as defined in claim 4, wherein said elements are located closely adjacent said holders so as to constitute thermal insulation between said elements and said holders.

14. The apparatus as defined in claim 13, wherein said elements are constituted by perforated metal plates.

15. The apparatus as defined in claim 14, wherein said elements are made of wire gauze.

16. The apparatus as defined in claim 4, further comprising means lodging said holders in respective first and second hermetically closed spaces that are separated from each other; the means lodging the holders including respective windows that allow at least a part of the radiation from said sources, located outside said respective spaces, to pass therethrough, and means for evacuating said spaces.

17. The apparatus as defined in claim 16, wherein said lodging means is a metal block that has means for maintaining the latter at a constant temperature.

* * * * *